United States Patent [19]

Vanderlaan et al.

[11] Patent Number: 4,798,807

[45] Date of Patent: Jan. 17, 1989

[54] MONOCLONAL ANTIBODIES AND METHOD FOR DETECTING DIOXINS AND DIBENZOFURANS

[75] Inventors: Martin Vanderlaan, San Ramon; Larry H. Stanker; Bruce E. Watkins, both of Livermore, Nina Rogers Bailey, Berkley, all of Calif.

[73] Assignee: The Regents of the University of California, Berkeley, Calif.

[21] Appl. No.: 877,909

[22] Filed: Jun. 24, 1986

[51] Int. Cl.$^4$ ............................................. G01N 33/53
[52] U.S. Cl. .................... 436/548; 436/815; 435/172.2; 435/948; 530/387; 530/808; 935/103; 935/105; 935/110
[58] Field of Search ................ 435/7, 28, 188, 172.2, 435/948; 436/548, 826, 815; 530/387, 808; 935/103, 105, 110

[56] References Cited

U.S. PATENT DOCUMENTS 4,238,472 12/1980 Albro ................................ 436/540
4,486,530 12/1984 David ..................................... 435/7
4,681,848 7/1987 Tsukamoto ........................ 935/103

OTHER PUBLICATIONS

Kennel-I, Chemical Abstracts 104: 181193z (1986).
Kennel-II, Chemical Abstracts 106: 16761s (1987).
Luster, Anal. Chem. 52, 1497–1500 (1980).
Kennel-I, Toxicology and Applied Pharmacology 82, 256–263 (1986).
Kennel-II, Chemosphere 15, pp. 2007–2010 (1986).

Primary Examiner—Robert J. Warden
Assistant Examiner—Robert Benson
Attorney, Agent, or Firm—Berthold J. Weis

[57] ABSTRACT

Compositions of matter are described which include five monoclonal antibodies that react with dioxins and dibenzofurans, and the five hybridomas that produce these monoclonal antibodies. In addition, a method for the use of these antibodies in a sensitive immunoassay for dioxins and dibenzofurans is given, which permits detection of these pollutants in samples at concentrations in the range of a few parts per billion.

2 Claims, 1 Drawing Sheet

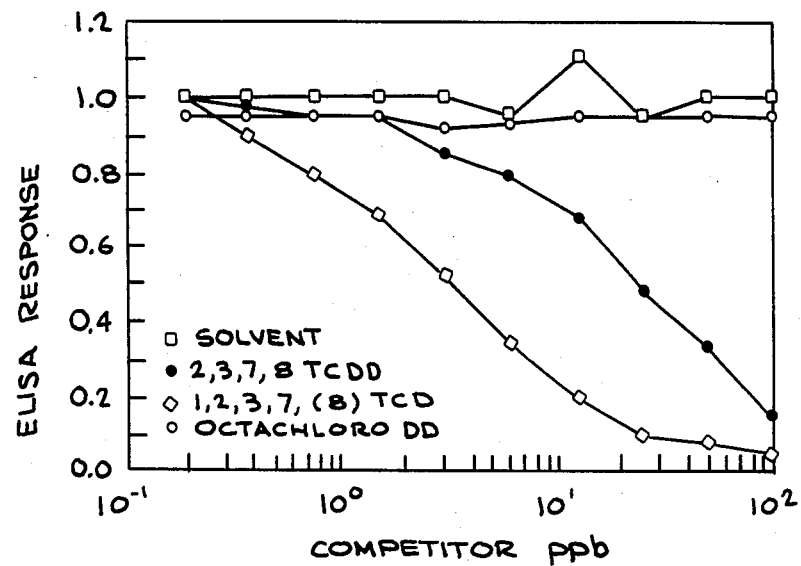

MONOCLONAL ANTIBODIES AND METHOD FOR DETECTING DIOXINS AND DIBENZOFURANS

The U.S. Government has rights to this invention pursuant to Contract No. W-7405-ENG-48 between the U.S. Department of Energy and the University of California, for the operation of Lawrence Livermore National Laboratory.

FIELD OF THE INVENTION

This invention relates to a method for the detection of dioxins and dibenzofurans, novel monoclonal antibodies useful in their detection and quantitative analysis, and hybridomas capable of producing said antibodies.

BACKGROUND OF THE INVENTION

Polychlorinated dibenzodioxins (PCDD) and dibenzofurans (PCDF) are persistent, toxic pollutants which pose a threat to both human health as well as the biosphere generally. These compounds are contaminants of herbicides, such as Agent Orange, and are also generated as by-products in a variety of industrial chemical processes, as well as in the course of combustion or incineration of other polychlorinated organics, such as plastics and polychlorinated biphenyls (PCB). In view of the extensive use or occurrence of such processes, dioxins and dibenzofurans are widespread in the environment. Now that the harmful nature of these materials has become fully recognized, it has become a matter of high priority to address the issue. An important, nontrivial first step is to identify sites of pollution, which requires a simple, economical, and rapid test for detecting the presence of these compounds in samples taken from soils, human or animal tissues, as well as foodstuffs.

An important aspect of a desirable test procedure relates to specificity. There are a large number of isomers both PCDD's and PCDF's, as well as PCB's, which vary in toxicity from very highly toxic to lesser toxicities, but which are also chemically similar to other, relatively harmless compounds. A second aspect of the problem is that the most toxic isomers of these compounds in the environment, i.e., 2,3,7,8-tetrachlorodibenzo-p-dioxin, is harmful in very small amounts, and is capable of being concentrated as it moves through food chains. Hence, a desirable test must be capable of detecting the presence of these harmful substances in very low concentrations. Chemical analysis of soil samples for contamination is also hampered by several other factors: (1) dioxins bind tightly to soil and show negligible solubility in water, and (2) the multiplicity of isomers and related chemical contaminants make quantitative assay by conventional gas chromatographic and mass spectrometric methods costly and time consuming. The costs and turn-around time preclude detailed sampling of an area to determine the extent of contamination, and require sophisticated centralized laboratories, unsuited for field monitoring of this health hazard.

THE PRIOR ART

The potential advantages of immunoassay procedures over conventional analytic methods have been recognized previously, in particular, that immunoassay offers a method which is as sensitive as gas chromatography and/or mass spectrometry, while being more rapid and less expensive.

One prior approach to the solution of the problem of detecting dioxins in the environment is discussed in a paper by P. W. Albro, et al, "Radioimmunoassay of Chlorinated Dibenzo-p-dioxins", Methods in Enzymology 84: 619–639, 1982 and U.S. Pat. No. 4,238,472, Albro et al, Radioimmunoassay for chlorinated Dibenzo-p-dioxins, Dec. 9, 1980. The assay described by Albro et al is a radioimmunoassay, based on polyclonal antisera produced by immunizing rabbits with 1-amino 3,7,8,-trichlorodibenzo-p-dioxin.

The Albro et al assay has not been widely applied since it has a number of limitations. It requires the frequent synthesis of $^{125}$I-TCDD, it requires three days to complete, and it is not sufficiently specific for the 2,3,7,8-TCDD because it uses nonspecific rabbit antisera.

Another approach is reported by Stephen J. Kennel et al in a paper entitled "Monoclonal Antibodies to Chlorinated Dibenzo-p-dioxins", Toxicology & Applied Pharmacology 82, 256–263, 1986. This test for dioxins is based on monoclonal antibodies produced by immunizing BALB/c mice with a thyroglobulin conjugate of dioxin, thyroglobulin-2-adipamide, 3,7,8-trichlorodibenzo-p-dioxin. Hybridomas were produced by cell fusion of immune spleen cells and myeloma cells called SP2/0, P3, or NSI. However, the test developed by Kennel et al suffers from the disadvantage of inadequate selectivity in that their antibodies fail to react with nonprotein conjugated 2,3,7,8,-tetrachlorodibenzo-p-dioxin in solution, the most toxic of the dioxin isomers and other dioxin isomers, while reacting with compounds which are not a target for identification. Other problems are that the test utilizes a radioimmunoassay procedure with iss attendant disadvantages.

OBJECTS OF THE INVENTION

The foregoing clearly indicates that there exists a continuing need for an effective, practical test for detecting toxic dioxins.

Accordingly, a major object of this invention is to provide an immunoassay method for dioxins, which will have the necessary selectivity and sensitivity to conclusively indicate the presence of dioxins in concentrations of a few parts per billion (nanograms per sample).

Another objective is to provide a test which can be carried out rapidly, which will be capable of being carried out in the field by a mobile facility.

Yet another object is to provide antibodies capable of conclusively recognizing the most toxic of the polychlorinated dioxins and dibenzofurans.

Another object is to define a procedure whereby sensitivity can be raised to achieve detection of toxins at the part per trillion level.

Additional objects, advantages and novel features of the invention wil be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention is an Enzyme-Linked-Immuno- sorbent-Assay ELISA procedure, whereby samples may be examined to determine the presence of polychlorinated dioxins and particularly 2,3,7,8-tetrachlorodibenzo-p-dioxin (TCDD), using unique monoclonal antibodies which are obtained from unique hybridoma cell lines, which will hereinafter be referred to as DD-1, DD-3, DD-4, DD-5 and DD-6. These hybridomas have benn placed in the public depository of the American Type Culture Collection (ATCC), Rockville, Md., and identified with the following accession numbers: DD-1, (HB 9741); DD-3, (HB 9742); DD-4, (HB 9743); DD-5, (HB9744); and DD-6, (HB 9745). The production of the cell lines and antibodies derived therefrom will be described in greater detail below. These antibodies are characterized by high affinity and selectivity toward TCDD. Their use with the proposed ELISA test protocol permits the determination of the presence of dioxins in test samples at levels of a few parts per billion and less. Tests can be completed in hours rather than days. The use of radio-labeled compounds is obviated. with the present antibodies, tests for TCDD can be conducted in aqueous media by sonication. In a preferred mode, the sensitivity of the present test procedure can be raised by the addition of detergents in concentration on the order of 0.05% by volume, making it possible to detect TCDD at levels down to the order of one part per trillion.

BRIEF DESCRIPTION OF THE DRAWING

The FIGURE shows competition ELISA data for antibody DD-1 when reacted with various concentrations of the competitors 2,3,7,8, TCDD, (closed circle); 1,2,3,7(8) TCDD (open diamond); octachloro DD (open circle) and solvent (open square).

DETAILED DESCRIPTION OF THE INVENTION

Production of the Hybridomas & Antibodies

The present hybridomas DD-1, DD-3, DD-4, DD-5, and DD-6 were produced by fusion of SP2/0 mouse myeloma cells with spleenocytes obtained from immunized BALB/c and Biozzi mice. In order for animals to respond immunologically to small organic molecules, the haptens (or analogs of them) must be conjugated to carrier proteins. The first step in producing antibodies, therefore, is to synthesize an analog with a functional group that can be attached to a protein. The TCDD analog chosen for this immunization was 1-amino-3,7,8,-trichlorodibenzo-p-dioxin (A-triCDD). This compound was synthesized according to a method published by Chae et al (1977) "Synthesis of 1-amino-3,7,8-trichlorodibenzo-p-dioxin and 1-amino-2,3,7,8-tetrachlorodibenzo-p-dioxin as Haptenic Compound", Agr. Food Chem., 25, 1207–1209. The A-triCDD can then be conjugated to carrier proteins, such as thyroglobulin, rabbit serum albumin (RSA), keyhole limpet hemocyane (KLH), and others. In our experiments, we used Bovine Serum Albumin (BSA). we then injected in BALB/c and Biozzi mice, as shown in the following table:

TABLE I

| Strain | Anti Dioxin Clones | |
|---|---|---|
| | Clone # | Isotype |
| Biozzi | DD-1 | IgG1 kappa |
| BALB/c | DD-3 | IgG1 kappa |
| Biozzi | DD-5 | IgG2a kappa |
| BALB/c | DD-4 | IgG2a kappa |

TABLE I-continued

| Strain | Anti Dioxin Clones | |
|---|---|---|
| | Clone # | Isotype |
| Biozzi | DD-6 | IgG2a kappa |

The immunization protocol followed typically involved 10 μg injections in adjuvant per month per mouse for a period of 10 months, with a final injection a few days prior to taking the animal's spleen.

After completion of the injection protocol, the spleen cells are removed and induced to grow in culture by fusing them with myeloma cells. In the present case, the spleenocytes were fused with the SP2/0 mouse myeloma cell line. These fused cells or hybridomas grow in culture and secrete monoclonal antibodies. Although each cell clone secretes only one type of antibody, from any given fusion of spleen cells typically 10,000 hybridomas are obtained. The screening procedure is therefore a matter of critical importance.

In this case the hybridomas were then screened for their ability to distinguish A-triCDD-BSA and A-triCDD-RSA from BSA and RSA. On the basis of this initial screen about 25 stable, antibody-producing colonies were isolated, subcloned, and frozen. The remaining clones were again screened for their abilities to recognize free TCDD in suspension. Experimentally, on the order of 10–100 nanograms of TCDD in hexane was dried, 0.5 ml of saline with BSA (1 mg/ml) was added and sonificated for 2 hrs. Experiments with $^{14}$C-TCDD showed that about half of the TCDD became suspended in the aqueous phase, corresponding to a concentration of about 100 ppb. Identical procedures were followed for other dioxin isomers. A dilution series in microtiter plate wells was then made with the suspended TCDD, antibody adde, and the competition ELISA completed. Competition ELISA test procedures are discussed in detail in the following reference: Butt, W. R. (1984) "Practical Immunoassay: The State of the Art", Marcel Dekker, Inc., N.Y., N.Y.

A large part of the success that we have had in characterizing the binding specificities of our monoclonal antibodies comes from having developed a reliable competition ELISA protocol. Our preferred assay starts from stock solutions at 10 ppm in hexane of the various compounds listed in Table I. 10 μl of hexane solution is aliquoted into a small vial, evaporated under a stream of nitrogen gas, and 500 μl of a 1 mg/ml solution of BSA in phosphate buffered saline with 0.1% BSA is added. The vial is capped and placed in an ultrasonic cleaning waterbath for two hours. Two hours of sonification gives a more reproducible assay than does an hour. During the sonification, the hexane appears to evaporate completely, and one is left with an aqueous solution containing the dioxin. Microtiter plates coated with A-triCDD-RSA are blocked with a three percent solution of ovalbumin and a two-fold dilution series of sonificated dioxin-BSA is then made, covering the range 100 ppb–0.1 ppb. In each well of the plate 100 μl of the sonificated dioxin-BSA solution is mixed with n equal volume of antibody. The antibody partitions between the dioxin adsorbed to the BSA, and the A-triCDD-RSA on the plate.

The FIGURE shows the results of a competition ELISA using monoclonal antibody DD-1, which is representative of our detailed procedure with other antibodies as well. A-TriCDD-RSA was adsorbed onto the surface of the wells of a microtiter plate. The various competitors listed were suspended in saline containing bovine serum albumin (BSA). These solutions were made by sonificating 10 μl of dioxin solution in hexane with 500 μl of saline-BSA. A dilution series of these dioxin-BSA solutions was then made covering the range of 100-0.2 ppb, and placed in the microtiter plate wells. An equal volume of DD-1 monoclonal antibody was then added, and allowed to react for 1 hour. Tne antibody binds either to the A-TriCDD-RSA on the plate or the dioxin in solution. After the hour, the solution phase is removed, the plate washed, and it is reincubated for an hour with peroxidase-conjugated goat-anti-mouse-immunoglobulins. A second washing is then done, and substrate (ABTS) added to the peroxidase. The enzyme-antibody conjugate and substrate function as a "developer", allowing the visualization of the DD-1 bound to the A-triCDD-RSA on the plate. Results are then expressed as a fraction of the response in wells with no competitor. In this example, DD-1 does not react with octachlorodibenzodioxin. At about 20 ppb of 2,3,7,8-TCDD the relative ELISA response is half of control, meaning that half the DD-1 antibody bound to the solution phase dioxin and half bound to the A-triCDD-RSA on the plate. For 1,2,3,7(8)-TCDD, 50% inhibition occurs at about 4 ppb, indicating the DD-1 prefers 1,2,3,7(8)-TCDD to 2,3,7,8-TCDD.

Based on this test, five hybridomas (named DD-1, DD-3, DD-4, DD-5 and DD-6) were selected for further study. Table II shows the specificity of these antibodies using this assay for a variety of dioxins, dibenzofuran, PCBs and other chlorinated hydrocarbons.

TABLE II

| Competitors | Monoclonal Antibodies $I_{50}$ ng | | | | |
|---|---|---|---|---|---|
| | DD-1 | DD-3 | DD-4 | DD-5 | DD-6 |
| 1,2,4-Tri-CDD | >200 | >200 | >200 | >10 | >200 |
| 2,3,7,8-TCDD | 1 | 3 | 5 | 0.5 | 6 |
| 1,3,7,8-TCDD | 0.2 | 0.15 | >2 | | 1 |
| 1,2,3,7,(8)-TCDD | 0.15 | 0.45 | 0.3 | 0.3 | 0.15 |
| 1,2,3,4,7-penta-CDD | >2 | >2 | >2 | | >2 |
| 1,2,3,7,8-penta-CDD | 0.2 | 0.15 | 0.02 | | >0.004 |
| 1,2,3,6(7),7(8),8(9)-hexa-CD[ | >200 | >200 | >200 | >10 | >200 |
| Octachloro-DD | >200 | >200 | >200 | >10 | >200 |
| 2,3,7,8-tetra-Bromo-DD | 0.05 | 1 | 1 | | >2 |
| 1-amino-2,7,8-TriCDD | 0.2 | >0.04 | >0.01 | >0.02 | 0.02 |
| 1-nitro-2,7,8-TriCDD | 0 | 0.15 | 0.02 | | >0.004 |
| Linker-triCDD | 0.17 | >0.04 | 0.2 | 0.15 | 0.05 |
| 2,3,7,8-TCDBF | 0.65 | 0.9 | 5 | 1 | 0.5 |
| 1,2,3,4,8,9-Hexa-CDBF | >200 | >200 | >200 | >10 | >150 |
| Octachloro-DBF | >200 | >200 | >200 | >10 | >200 |
| 2,2',4,6-TCBP | >200 | >200 | >200 | >10 | >200 |
| 3,3',4,4'-TCBP | >200 | >200 | >200 | >10 | 100 |
| 2,2',3,4,5-Penta-CBP | >200 | >200 | >200 | >10 | >200 |
| 2,2',3,4,4',5-Hexa-CBP | >200 | >200 | >200 | >10 | >200 |
| 2,2',3,4,5,5',6-Hepta-CBP | >200 | >200 | >200 | >10 | >200 |
| 2,2',3,3',4,4',6-Hepta-CBP | >200 | >200 | >200 | >10 | >200 |
| 2,2',3,3',4,5,6,6'-Octa-CBP | >200 | >200 | >200 | >10 | >200 |
| 2,2',3,3',4,4',5,5'-Octa-CBP | >200 | >200 | >200 | >10 | >200 |
| Pentachlorophenol | >2000 | >2000 | >2000 | >2000 | >2000 |
| 2,4-Dichlorophenol | 2000 | >2000 | >2000 | >2000 | >2000 |
| 2,4,5-Trichlorophonol | 800 | >2000 | >2000 | >2000 | >2000 |
| 4,5-Dichlorocatechol | 2000 | >2000 | >2000 | >2000 | >2000 |
| 2,4-Dichloro-6-nitrophenol | >2000 | >2000 | >2000 | >2000 | >2000 |
| 2,2,2-Tricholoroethanol | >2000 | >2000 | >2000 | >2000 | >2000 |
| Aldrin | >2000 | >2000 | >2000 | >2000 | >2000 |
| BHC | 300 | >2000 | >2000 | >2000 | >2000 |
| DDT | >2000 | >2000 | >2000 | >2000 | >2000 |
| Chlordane | >2000 | >2000 | >2000 | >2000 | >2000 |
| Endrin | >2000 | >2000 | >2000 | >2000 | >2000 |
| Heptachlor | >2000 | >2000 | >2000 | >2000 | >2000 |
| Toxaphene | nd | >2000 | >2000 | >2000 | >2000 |
| Endosulfan | >2000 | >2000 | >2000 | >2000 | >2000 |
| Kepon | >2000 | >2000 | >2000 | >2000 | >2000 |
| 2,5-Dichloronitrobenzene | 90 | 2000 | >2000 | 2000 | 700 |
| 2,4,5-Trichlorophenoxyacet | 2000 | >2000 | >2000 | >2000 | 2700 |
| Chlorobenzene | >2000 | >2000 | >2000 | >2000 | >2000 |
| 2,4-Dichlorophenoxyacetic | >2000 | >2000 | >2000 | nd | nd |

The FIGURE and Table II show representative competition data using several chlorinated compounds as competitors. From such data, one can determine the concentration required to inhibit antibody binding by 50% ($I_{50}$). Table II lists the $I_{50}$ for all compounds tested with the antibodies. In reporting these values, factors of two are about the limit of significance. All six antibodies have highest affinity for tetrachlorodibenzodioxins, with highest affinity for the mixed 1,3,7,8, isomer. They have slightly less affinity for the 2,3,7,8-TCDD and 2,3,7,8-TCDBF. DD-4 has some reactivity with the 1,2,3,6,7,8-hexa-CDD. Up to the highest concentration tested (100 ppb) all antibodies either do not react or react only marginally with hexachloroDBF, octochloro-DBF, octachloro-DD, and PCB's. The binding specificities of these antibodies are highly desirable, since they prefer the most toxic of the dioxin and dibenzofuran isomers.

It is our experience that different mice will produce clones with different binding specificity and affinity. Each mouse appears nearly unique in the way it responds to an immunogen. Multiple clones from the same mouse are often quite similar. As such, we were interested in deriving a set of monoclonal antibodies from different mice. we have selected five hybridomas, from different mice using the same basic protocol. All recognize 2,3,7,8-TCDD. These assays are highly reproducible, with replicate assays on TCDD the $I_{50}$ value varied less than 20%.

SAMPLE ANALYSIS

The test procedures for determining the presence of dioxins and dibenzofurans is in principle again a competition ELISA test using the antibodies described in the specification above. The samples may be soil samples, tissue samples, or food samples. These samples are initially pretreated in order to extract the dioxins or dibenzofurans and quantitatively transfer them into a medium suitable for use in the immunoassay scheme.

Soil samples, for example, are treated according to the following protocol. Initially, the dioxins or dibenzofurans are extracted into a hexane in accordance with the standard EPA method 613. At this point, the extract is put through one or more clean-up steps to remove interfering substances, as discussed in greater detail below. Thereafter, the sample is concentrated near dryness. At this juncture, the sample residue is resuspended in saline solution. It has been found that reproducible and reliable results are obtained by sonification of the saline solution for about 2 hours, leading to satisfactory determinations capable of identifying the presence of toxins in the part per billion range.

The sensitivity can be dramatically improved by the addition of controlled quantities of detergent. Our preferred detergents are Cutscum TM and Tween-20. We have found that, by reducing the concentration of these detergents to about 0.05% by volume, it is possible to remarkably improve the sensitivity of the assay to detect dioxins or dibenzofurans at concentrations as low as a few parts per trillion.

The remainder of the procedure is carried out by placing the sample on the microtiter plate, adding the antibody, proceeding with the competition ELISA assay, collecting and analyzing the data by microcomputer. The procedure is further illustrated by the following examples.

EXAMPLE I 10 grams of wet soil is weighed into a 500 ml amber bottle and is thoroughly mixed with 20 grams of sodium sulfate. 20 ml of methanol and 150 ml of hexane are added and the mixture is shaken for at least 3 hours. The hexane layer is decanted from the mixture, filtered and the volume reduced to 1 ml on a rotary evaporator. The residue is applied to a short, disposable chromatography column (silica or alumina, 1 gram) and eluted with either hexane or 20% methylene chloride/hexane, respectively. The solvent is then removed by a stream of dry nitrogen gas and the residue is suitable for incorporation into the immunoassay scheme.

The purpose of the chromatography column is to remove any extraneous material in the soil which may interfere with the assay. Soils may contain a large amount of hexane soluble, organic material in which the dioxin may partition in preference to the solvent used in the immunoassay rendering the dioxin inaccessible to the antibodies. without the chromatography, the immunoassay will not work with some soil types. The above two conditions both work equally well and others should as well. This procedure should work equally well on tissue and food samples.

EXAMPLE II

The soil extract or test compound dissolved in hexane is dryed and 5 microliters of a 5% (v/v) solution of detergent in methanol (e.g., Cutscum TM) is added. The methanol is then evaporated by a stream of $N_2$. 500 microliters of Phosphate Buffered Saline [0.01 M phosphate, 0.1 M NaCl, pH 7.2] (PBS-7) is then added and the reaction vial tightly capped. The vial is then placed in a Bransonic 220 ultrasonic cleaner and sonificated for 30 minutes. This material is then titered for dioxin content in a competition ELISA.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. Hybridomas deposited at the American Type Culture Collection under ATCC accession numbers as follows, identified as DD-1 (HB 9741); DD-3, (HB 9742); DD-4, (HB 9743); DD-5, (HB 9744); and DD-6, (HB 9745); which secrete monoclonal antibodies which bind dibenzo-p-dioxins and dibenzofurans.

2. A monoclonal antibody produced by a hybridoma selected from the group consisting of hybridomas identified as DD-1, DD-3, DD-4, DD-5, and DD-6 and deposited at the American Type Culture Collection under ATCC accession numbers (HB 9741), (HB9742), (HB 9743), (HB 9744), and (HB 9745), respectively.

* * * * *